United States Patent [19]

McGredy

[11] Patent Number: Plant 5,850

[45] Date of Patent: Jan. 13, 1987

[54] ROSE PLANT

[76] Inventor: Samuel D. McGredy, 130 B Beach Rd., Castor Bay, Auckland 9, New Zealand

[21] Appl. No.: 724,965

[22] Filed: Apr. 19, 1985

[51] Int. Cl.[4] ..... A01H 5/00

[52] U.S. Cl. ..... Plt./8

[58] Field of Search ..... Plt./7-8

*Primary Examiner*—R. E. Bagwill
*Attorney, Agent, or Firm*—Vincent G. Gioia

[57] ABSTRACT

A new miniature rose variety of orange-gold flower coloring and disease resistant, hardy plant.

1 Drawing Figure

The present invention relates to a new and distinct variety of rose plant of the minature rose class, which was originated by my crossing as seed parent the rose known as "Sea Spray" and as pollen parent the rose known as "Dorola". The varietal denomination of this new variety is "Freegold".

Among the novel characteristics possessed by this new variety which distinguish it from its parents and all other varieties of which I am aware are its attractive orange-gold colored flowers which retain their color well and a disease resistant, hardy plant of good vigor. Flowers are long lasting on the plant and as cut flowers. Asexual reproduction by budding of the new variety as performed in Clackamas County, Oreg., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "22A" is plate 22A of The Royal Horticultural Society Colour Chart.

Parentage: Seedling.
*Seed parent.*—"Sea Spray".
*Pollen parent.*—"Dorola".
Class: Miniature.

The following observations are made of specimens grown outdoors in Clackamas County, Oreg., during the month of July.

FLOWER

Blooming habit: Near continuous.

A. Bud:
- (1) *Size.*—Small (1¼ to 1½ inches).
- (2) *Form.*—Long pointed.
- (3) *Color.*—When sepals first divide — near 22A. When petals begin to unfurl — the varied color tonality becomes evident. Main coloring appears 26B to C, however shading of 22A-D may also be seen.

- (4) *Sepals.*—Longer than bud, glaborous outside, wooly inside and on margins, near 144A.
- (5) *Peduncle.*—Length — about 1¼ inch. Aspect — straight. Strength — erect. Color — near 144A, smooth with scattered glandular hairs.

B. Bloom:
- (1) *Size.*—Average size when fully expanded — about 1¼ to 1½ inches.
- (2) *Borne.*—Singly and sprays of three to seven florets.
- (3) *Form.*—High centered, becoming flat, outer petals reflex, stamens show.
- (4) *Petalage.*—Number of petals under normal conditions — about 20 to 25.
- (5) *Color.*—After sepals fall and as petals unfurl, varied yellow-orange flower coloring appears. Coloring appears deeper toned in bud form than in open bloom, varying from yellow ochre 22D to chrome yellow 14D in open bloom stage. As flowers age, some orange red washing, near 33D, becomes evident, particularly on outer segments of petal top surfaces. Yellow tones are more visible on inner petals, particularly at the lower petal segments toward the point of petal attachment. Flower centers change from orange yellow when stamens are fresh to brownish yellow upon aging.

C. Petals:
- (1) *Texture.*—Thick.
- (2) *Appearance.*—Inside — satiny, outside — satiny.
- (3) *Form.*—Deltoid, acuminate.
- (4) *Arrangement.*—Regularly arranged, shingle-like.
- (5) *Petaloids in center.*—Few 5 or less.
- (6) *Persistence.*—Drop off cleanly.
- (7) *Fragrance.*—Slight.
- (8) *Lasting quality.*—Very long lasting on plant and as cut flower.

REPRODUCTIVE ORGANS

A. Stamens, filaments and anthers:
- (1) *Arrangement.*—Unequal length, arranged around styles.
- (2) *Color.*—Filaments near 12A, anthers 15A.

B. Pollen:
- *Color.*—Near 15A.

C. Styles: Short, few, with large stigmas, near 12D.

D. Stigmas:
- *Color.*—Near 12D.

E. Hips: Long oval, carpels few, ⅜ inch, near 15A when mature, seeds do not protrude.

PLANT

A. Form: Compact, upright.
B. Growth: Uniform, free blooming.
*Height attained.*—About 24 inches.
C. Foliage: Compound 5 leaflets.
(1) *Size.*—Medium.
(2) *Quantity.*—Abundant.
(3) *Color.*—New foliage: Upper side — near to 146A. Under side — near to 147C. Old foliage: Upper side —near 137A. Under side — near 138A.
(4) *Shape.*—Oval, pointed.
(5) *Texture.*—Upper side is shiny, slight veining and under side is satiny.
(6) *Edge.*—Serrated.
(7) *Serration.*—Fine.
(8) *Leaf stem.*—Color — near 146A. Under side — near 147C.
(9) *Stipules.*—Very long, bearded.

(10) *Resistance to disease.*—Blackspot — excellent. Mildew — excellent. Rust — excellent.
D. Wood:
(1) *New wood.*—Color — near 144C. Bark — smooth, waxy.
(2) *Old wood.*—Color — near 144A. Bark — smooth.
E. Thorns:
(1) *Thorns.*—Quantity (main stalk): ordinary. On laterals from stalk — few. Form — narrow, flat base. Length — long. Color — near 144D. Position — irregular, scattered.
(2) *Prickles.*—None.
F. Winter Hardiness: Hardy.

I claim:

1. A new and distinct variety of rose plant of the miniature rose class, substantially as shown and described, characterized particularly by orange-gold flowers with almost no tendency to fade but with orange red brushing on petal top surface as flowers age borne on an attractive, disease resistant, hardy plant.

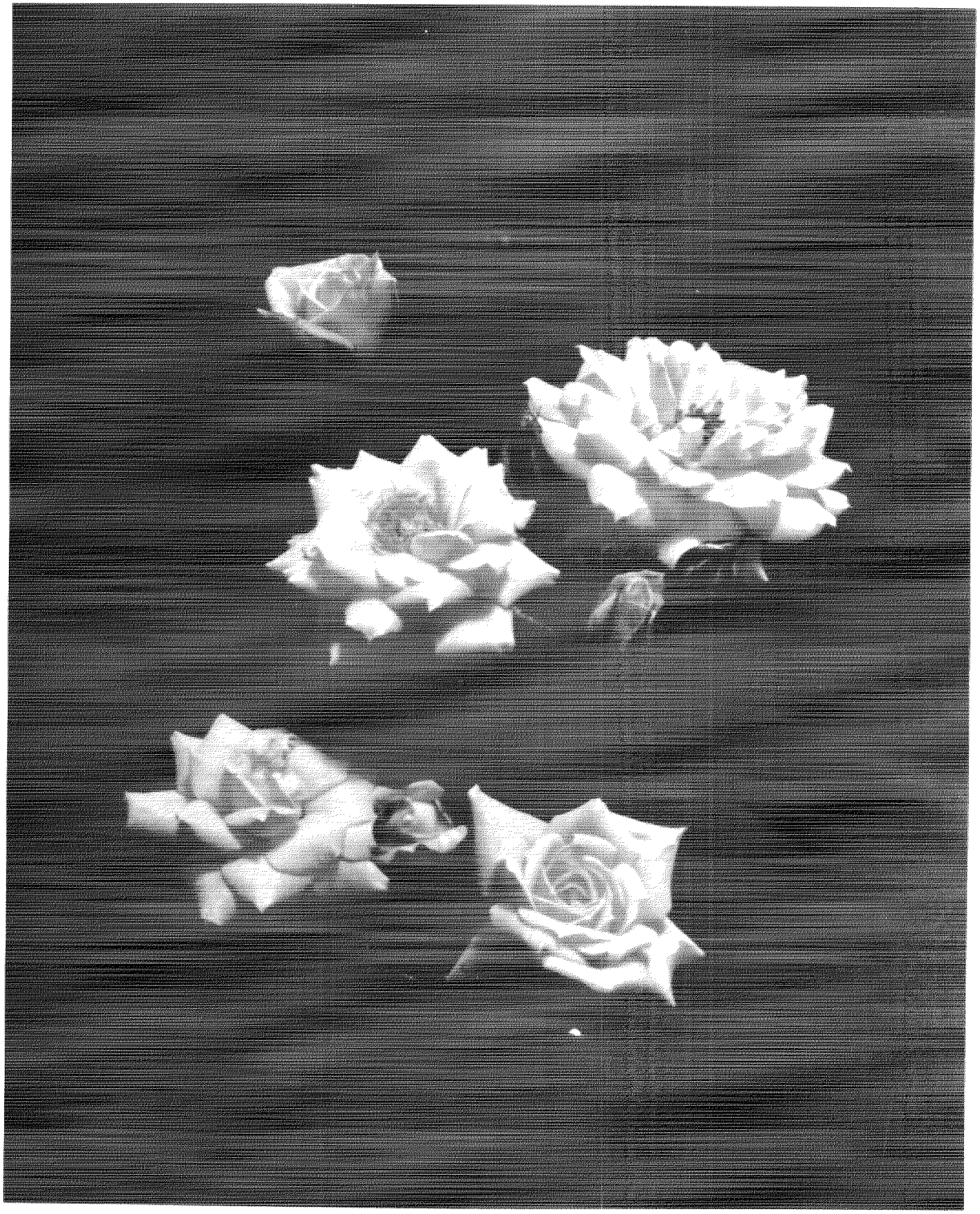

* * * * *